United States Patent [19]

Daniel et al.

[11] Patent Number: 5,437,630
[45] Date of Patent: Aug. 1, 1995

[54] ARTHROSCOPIC CUTTER HAVING CURVED ROTATABLE DRIVE

[75] Inventors: Sean C. Daniel, San Francisco; Andrew J. Juknelis, San Jose; Barry J. Kauker, Soquel, all of Calif.

[73] Assignee: Stryker Corporation, Kalamazoo, Mich.

[21] Appl. No.: 313,407

[22] Filed: Sep. 27, 1994

Related U.S. Application Data

[63] Continuation of Ser. No. 144,195, Oct. 27, 1993, abandoned.

[51] Int. Cl.⁶ .............................................. A61B 17/20
[52] U.S. Cl. ..................................... 604/22; 606/170; 606/180
[58] Field of Search ................. 128/56, 751, 752, 755; 433/102, 103, 112, 114, 124, 127, 131; 604/22; 606/170, 180

[56] References Cited

U.S. PATENT DOCUMENTS

| | | | |
|---|---|---|---|
| 412,920 | 10/1889 | Reynolds | 433/112 |
| 2,093,682 | 9/1937 | Levy | 433/124 |
| 3,678,934 | 7/1972 | Warfield et al. | |
| 3,732,858 | 5/1973 | Banko | |
| 3,844,272 | 10/1974 | Banko | |
| 3,882,872 | 5/1975 | Douvas et al. | |
| 3,945,375 | 3/1976 | Banko | |
| 3,990,453 | 11/1976 | Douvas et al. | |
| 3,995,619 | 12/1976 | Glatzer | |
| 3,996,935 | 12/1976 | Banko | |
| 4,014,342 | 3/1977 | Staub et al. | |
| 4,167,944 | 9/1979 | Banko | |
| 4,203,444 | 5/1980 | Bonnell et al. | |
| 4,210,146 | 7/1980 | Banko | |
| 4,246,902 | 1/1981 | Martinez | |
| 4,274,414 | 6/1981 | Johnson et al. | |
| 4,368,734 | 1/1983 | Banko | |
| 4,512,344 | 4/1985 | Barber | |
| 4,517,977 | 5/1985 | Frost | |
| 4,598,710 | 7/1986 | Kleinberg et al. | |
| 4,646,736 | 3/1987 | Auth | 606/170 |
| 4,646,738 | 3/1987 | Trott | |
| 4,649,919 | 3/1987 | Thimsen et al. | |
| 4,681,541 | 7/1987 | Snaper | |
| 4,811,734 | 3/1989 | McGurk-Burleson et al. | |
| 4,819,635 | 4/1989 | Shapiro | |
| 4,834,729 | 5/1989 | Sjostrom | |
| 4,842,578 | 6/1989 | Johnson et al. | |
| 4,923,441 | 5/1990 | Shuler | |
| 4,986,825 | 1/1991 | Bays et al. | |
| 5,007,917 | 4/1991 | Evans | |
| 5,061,238 | 10/1991 | Shuler | |
| 5,152,744 | 10/1992 | Krause et al. | |
| 5,160,318 | 11/1992 | Shuler | |
| 5,192,292 | 3/1993 | Cezana et al. | |

FOREIGN PATENT DOCUMENTS 2362157  11/1974  Germany.

OTHER PUBLICATIONS

Stryker Brochure 270-701-11 including Model #270-851 entitled "The Elite Arthroscopy Power System".

(List continued on next page.)

Primary Examiner—C. Fred Rosenbaum
Assistant Examiner—N. Kent Gring
Attorney, Agent, or Firm—Flynn, Thiel, Boutell & Tanis

[57] ABSTRACT

A powered rotatable surgical tissue working tool for chucking in a powered rotating surgical handpiece includes a tubular elongate outer member having a distal tip portion angled off the central axis of the proximal portion of such tubular outer member, by reason of an angled portion therebetween. A rotatable elongate inner member extends coaxially and rotatably within the tubular outer member and has a rotatably drivable proximal portion, a distal tip portion for tissue working interaction with the distal tip portion of the outer member, and a flexibly bendable portion therebetween rotatably housed within the angled portion of the outer member. An annular space between the inner and outer member communicates between the distal tip portions thereof and the handpiece for permitting suction withdraw of flowable materials from a surgical site axially through such annular space and to a suction source. The annular space is maintained between the flexible portion of the inner member and the angled portion of the outer member despite rotation of the inner member.

18 Claims, 6 Drawing Sheets

OTHER PUBLICATIONS

Baxter Brochure entitled "We've Expanded Our Line So You Can Reduce Yours" 1990 (2 pages).

Smith & Nephew (Dyonics) Brochure entitled "Extending Your Arthroscopic Reach" 1979 (4 pages).

Storz Brochure entitled "Precision Arthroplasty System", No. SPA-1170 (4 pages).

Storz Brochure entitled "Meet the Lightweight Heavyweight Arthro-Ease", (3 pages).

Storz Brochure entitled "The Large Joint and Microarthroplasty System . . . " (2 pages—with attached 2 page price list).

Storz Brochure entitled "We Know the Importance of Staying Sharp!", No. 1188-2500-A115 (2 pages).

Baxter brochure entitled "The Powercut TM Surgical System", No. 104-01-88-Ortho (3 pages).

Dyonics Brochure entitled "Dyonics Disposable Blades are the Right Tools", 1989, No. P/N 1060112 (3 pages).

Concept Brochure entitled "Intra-Arc® Drive System", No. 812388 (4 pages).

Zimmer Brochure entitled "Big on Performance", No. 97-3000-324 (4 pages).

Bowen Brochure entitled "Advances in Arthroscopy" (4 pages) and photo A and sketch B showing the Bowen angle-headed rotary cutter.

ARTHROSCOPIC CUTTER HAVING CURVED ROTATABLE DRIVE

This application is a continuation of U.S. Ser. No. 08/144,195, filed Oct. 27, 1993, now abandoned.

FIELD OF THE INVENTION

This invention relates to a rotatable surgical tool drivable by a powered rotary surgical handpiece and useable for arthroscopic surgery.

BACKGROUND OF THE INVENTION

U.S. Pat. No. 5,192,292 (Cezana et al), assigned to the Assignee of the present invention, discloses a straight, or linear, rotatable arthroscopic tool and a powered rotary surgical handpiece for releasably chucking and rotatably driving such tool. The tool comprises a tubular outer member having a hollow base at its proximal end for releasably fixed chucking on the handpiece, an elongate, slim, tubular intermediate portion, or sleeve, fixedly extending forward from said base and having a distal tip portion terminating the distal end of the sleeve. The tool further comprises a rotatable inner member having a proximal end portion defining a hub for rotational driving by a rotor of the handpiece when the tool is chucked in the handpiece. The rotatable inner member further comprises an intermediate portion extending forward from and rotatable in fixed relation with the hub and ending in a distal tip portion. The hub protrudes rearwardly from the tubular outer member, whereas the intermediate portion and distal tip portion of the rotatable inner member are sleeved within the tubular outer member. The distal tip portion of the rotatable inner member lies within and is rotatable within the distal tip portion of the tubular outer member. The distal tip portions are provided with means for surgically working tissue of a patient at a surgical site on the patient. The tissue working means may for example, comprise coacting oval shearing slots, or windows, on the distal tip portions. In one unit according to the aforementioned patent, a toothed shearing edge on the inner member slot coacts in a shearing fashion with a cutting edge on the outer member slot.

In the tool disclosed in the aforementioned U.S. Pat. No. 5,192,292, the rotatable inner member is tubular and open from the distal tip portion thereof through the intermediate portion and to a location on the hub in communication through the handpiece with a suction source, for suctioning flowable material, including irrigation liquid and pieces of tissue, from the surgical site.

In this prior patented device, the hollow tubular inner member is snugly, though rotatably, supported within the tubular outer member such that the flow of suctioned flowable material from the surgical site to the handpiece is inside the hollow tubular inner member. Further, the inner and tubular outer member are substantially rigid so that both are necessarily straight, to allow rotation of the inner member within the outer member.

The present assignee, Stryker Corporation, under model designation 270-851, has for several years manufactured a tool generally similar to that described above but wherein the above-mentioned coacting shearing slots are absent. The rotatable inner member carries a burr at its distal end exposed through the open front end of the outer tubular member, and the inner rotatable member has a solid shaft of maximum diameter substantially less than the interior diameter of the outer tubular member so as to provide an annular clearance therebetween. The intermediate portion of the inner shaft is supported by several axially spaced bushings distributed along its length and supported by the interior wall of the outer tubular member. Such bushings are provided with axially extended grooves which are open radially and endwise to allow suction of flowable materials from the surgical site along the length of the tool to the handpiece radially between the shaft and the inner wall of the outer tubular member. Again, the outer tube and inner shaft are both rigid and are thus necessarily straight to allow relative rotation.

U.S. Pat. No. 5,152,744 (Krause et al), assigned to Smith and Nephew Dyonics, discloses a tool in which the rigid outer tubular member is curved near its distal end, so that the distal end is angled from the intermediate portion of the tool. The rotatable inner member is a hollow tubular member closely rotatably supported for rotation within the outer tubular member. The inner tubular member, adjacent its distal end, and in the curved portion of the outer tubular member, is purportedly made flexible enough to rotate within the curved outer tube in several alternative ways. In one embodiment, Krause reduces the diameter of the purportedly flexible portion and perforates it with closely axially and circumferentially spaced holes. Alternatively, Krause makes this portion purportedly flexible enough to rotate within the curved outer tube, by cutting therein axially and circumferentially close spaced, circumferentially extending, elongate chordal slots, the slots being connected by narrow circumferential and axial webs. The slots each extend almost halfway through the diameter of the inner tube. Axially adjacent pairs of these chordal slots are angularly shifted through 90° with respect to each other. In a further embodiment, the purported flexibility sufficient to enable rotation of the inner tube within the curved portion of the outer tube is to be achieved axially close spaced, radially planar slots cut almost all the way through the thickness of the inner tubular member, leaving only a narrow web of axially extending tube material between the circumferential ends of each slot, and wherein axially alternate slots open in diametrically opposite directions, the slots each being filled and hence closed with a web of silicone rubber to prevent leakage of flowable material radially out of the flexible portion of the rotatable inner tube.

U.S. Pat. No. 4,646,738 (Trott), assigned to Concept, Inc., rather similarly discloses a curved tubular outer member snugly rotatably supporting therein a hollow tubular inner member. The latter has a purportedly flexible portion in the curved zone of the tubular outer member, and comprising a set of three spirally wound tubes of flat metallic ribbon which are disposed one within the other to provide inner, middle and outer spirally wound tubes. The inner, middle and outer spirals are wound in alternating opposite directions and are spot welded at each end to form a composite three-layer purportedly flexible tube. Torque applied to one end of such composite flexible tube is to be transmitted by alternate layers trying to expand (unwind) or trying to contract (wind up) such that the middle spiral is to either attempt to expand and be resisted by contraction of the outer layer or the middle spiral is to attempt to contract or wind up and be resisted by the inner spiral. Further, the three spirals are welded to each other by spot welds disposed longitudinally along the spirally wound composite tube.

Accordingly, the objects and purposes of the present invention include provision of a tool drivable by a powered rotative surgical handpiece, wherein the tool has a fixed outer tubular member with an angled portion near the distal end thereof and inner rotatable member with a flexible portion at the angled portion of the outer member, in which such tool overcomes apparent difficulties of the prior art, including avoiding excessive friction between angled, snugly radially telescoped inner and outer tubes during rotation of the inner tube, high torque and power expenditures, excessive heating, friction and heat induced fatigue or wear, cost and complexity and unreliability of manufacture of hollow flexible tube portions, possible migration of hard (e.g. bone) fragments into flexible inner rotor slots (which may impede closing thereof and hence flexing) and through such slots into a close clearance rotative interface between inner and outer members so as to upset rotating clearances therebetween, inability to withdraw the inner member rearwardly out of the outer member and replace same forwardly into the outer member, and the like.

SUMMARY OF THE INVENTION

A powered rotatable surgical tissue working tool, for chucking in a powered rotating surgical handpiece. The tool includes a tubular elongate outer member having a distal tip portion angled off the central axis of the proximal portion of such tubular outer member, by reason of an angled portion therebetween. A rotatable elongate inner member extends coaxially and rotatably within the tubular outer member and has a rotatably drivable proximal portion, a distal tip portion for tissue working interaction with the distal tip portion of the outer member, and a flexibly bendable portion therebetween rotatably housed within the angled portion of the outer member. An annular space between the inner and outer member communicates from the distal tip portions thereof to the handpiece for permitting suction withdraw of flowable materials from a surgical site axially through such annular space and to a suction source. The annular space is maintained between the flexible portion of the inner member and the angled portion of the outer member despite rotation of the inner member.

Other objects and purposes of the invention will be apparent to those familiar with apparatus of this general kind upon reading the following specification and inspecting the accompanying drawings.

DETAILED DESCRIPTION OF THE INVENTION

A tool 10 (FIGS. 1 and 2) embodying the invention is adapted for chucking in a powered rotating surgical handpiece of any desired kind, an example which is disclosed in above-mentioned Cezana et al U.S. Pat. No. 5,192,292, (assigned to the assignee of the present invention). Such a handpiece is schematically indicated at HP in FIG. 2. The handpiece HP has a housing H fixedly containing a suitable rotary drive motor means, indicated in broken lines at MM (for example electrically or fluid powered). The motor means MM has a rotary output shaft SH extending forward therefrom and fixedly carrying at its front end a diametrally protruding drive pin DP (FIG. 2). Although the handpiece HP may contain a suitable power source, such as electric batteries, in the example shown, same is connectible to a suitable remote power source P, for example electrical power source or a pressure gas source. The handpiece HP also preferably includes a connection to a suitable suction source S.

The tool 10 comprises a tubular outer member 11 (FIG. 2) comprising a proximal hollow base 12. An elongate tubular sleeve 13 is fixedly telescoped in and extends coaxially forwardly from the hollow base 12. The sleeve 13 includes a distal tip portion 14 and an intermediate portion 15 extending from the base 12 toward the distal tip portion 14. The sleeve 13 is here a rigid, thin walled, constant diameter, circular cross-section tube of stainless steel or equivalent material. The base 12 is configured to be rearwardly insertable in, fixedly held by, and releasably removable forward from a chuck C on the forward end of the handpiece HP. To cooperate with the chuck of the handpiece shown in above-mentioned U.S. Pat. No. 5,192,292, the base 12 (FIGS. 1 and 2) includes on its surface an annular groove 20 forward of a rearwardly opening, generally funnel shaped slot 21. Upon rearward insertion of the tool 10 into the handpiece HP (rearward insertion of the base 12 into the chuck C) of U.S. Pat. No. 5,192,292, the base slot 21 receives a radially inward extending fixed pin in the chuck C, which fixes the outer member 11 against rotation in the handpiece HP. Simultaneously, the annular groove 20 in the outer member base 21 receives diametrically opposed half rings 23 in the chuck. The half rings are diametrically biased toward each other by spring means 24 in the chuck C, as schematically indicated in FIG. 2, to axially fix the outer member base 21 with respect to the handpiece HP. The handpiece HP includes means, not shown, manually actuable to pull apart the half rings 23 to thereby allow tool 10 to be pulled forwardly out of the handpiece chuck C after surgery, or during surgery when it is desired to substitute a different tool into driving relationship with the handpiece HP.

Figure 1:
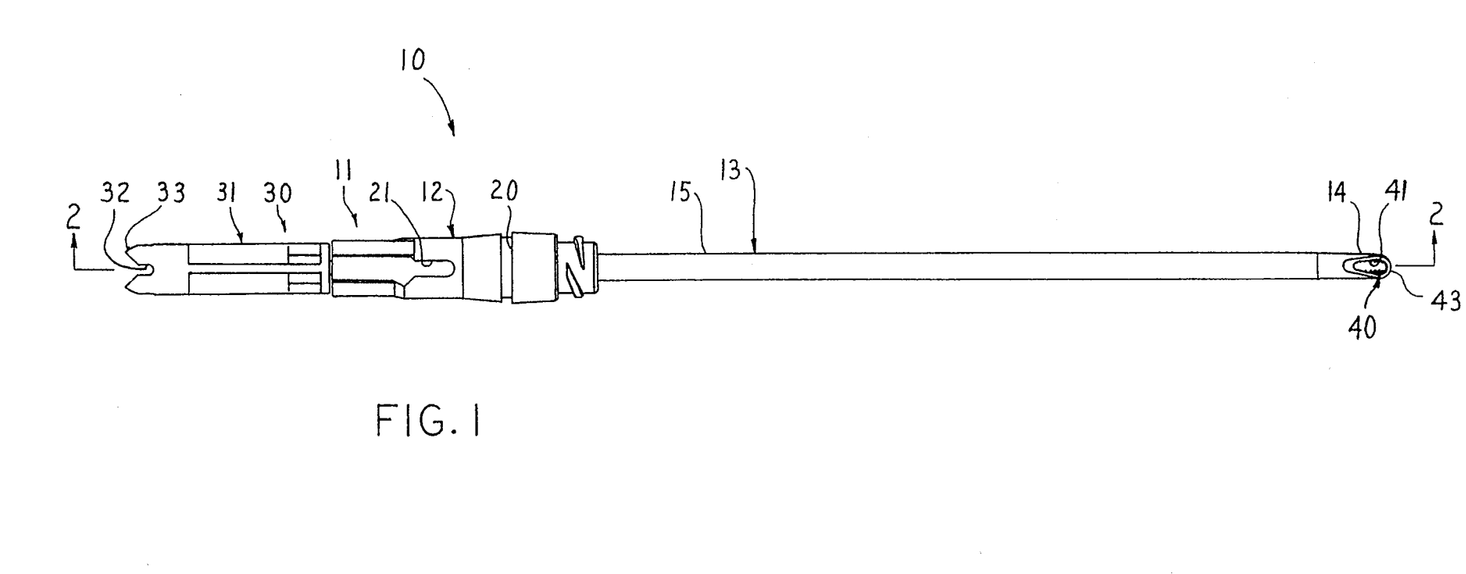
FIG. 1 is a top view of a tool embodying the invention.
Figure 2:
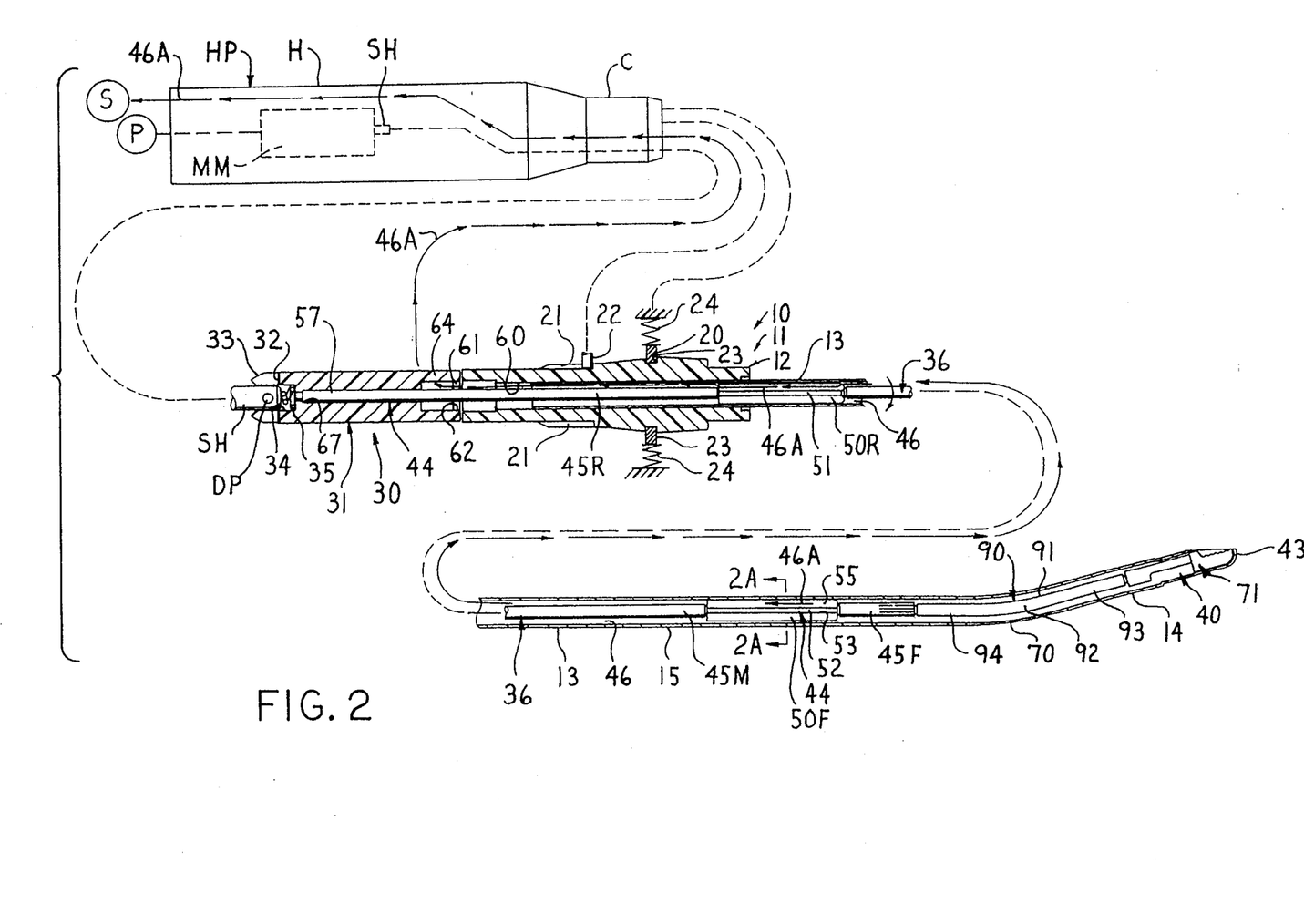
FIG. 2 is an enlarged fragmentary central cross sectional view substantially taken on the line 2—2 of FIG. 1 and showing schematically the cooperating parts of a corresponding handpiece.

A driven rotatable elongate inner member 30 extends coaxially and rotatably within the tubular outer member 11 (FIGS. 1 and 2). The rotatable inner member 30 has a proximal end portion, defining a hub 31 rotatably drivably engageable by the rotary handpiece shaft SH and its transverse drive pin DP. More particularly, in the embodiment shown, the hub 31 includes at least two (here four) diametrally opposed, evenly circumferentially distributed, rearward opening notches 32 circumferentially spaced by a corresponding number of rear extending fingers 33. The notches 32 and fingers 33 surround and extend rearward from a central, blind, rear opening recess 34 (FIG. 2) in the hub 31. A coil compression spring 35 (FIG. 2) is snugly housed in the recess 34 and extends rearward therefrom.

The rotatable inner member 30 has an intermediate portion 36 (FIG. 2) coaxially fixed to and extending forward from the hub 31. The rotatable intermediate portion 36 is supported for rotation within the intermediate portion 15 of the tubular outer member 11 in a manner hereafter discussed. The rotatable inner member 30 has a distal tip portion 40 fixed forward of the intermediate portion 36 for rotation therewith and snugly rotatably disposed within the distal tip portion 14 of the tubular outer member 11.

The distal tip portions 14 and 40 here have means, hereafter discussed more fully, for surgically working the tissue of a patient at a surgical site on the patient. Tools of the herein described type can be provided with a variety of different purpose surgical tissue working means including burrs, cutters, etc. of conventional type. In the FIGS. 1 and 2 example, the distal tip portion 14 of the outer tubular member 11 is provided with an angled, laterally and somewhat forwardly opening, planar window 41. The window 41 has laterally opposed cutting edges. The window 41 may be so formed by forming the distal tip portion of the tubular outer member with a semi-spherical closed end and then machining away a part thereof in an angled planar manner as here shown in FIGS. 1 and 2. The inner distal tip 40 is rotatable snugly within the outer distal tip portion 14 and has a cutting edge 42 rotatable in shearing relation past the cutting edge of the window 41.

The inner member 30 is axially insertable forwardly into the tubular outer member 11 and is axially rearwardly removable therefrom when not installed on a handpiece HP. On the other hand, when installed on a handpiece HP, by rearward insertion into the forward extending chuck C thereof, the forward end of the shaft SH of the handpiece partly compresses the spring 35 (FIG. 2) of the inner member hub 31, to push the inner distal tip portion 40 forward snugly against the front end 43 of the distal tip portion 14 of the outer member 11, so as to axially accurately position the rotatable inner tip portion 40 with respect to the outer tip portion 14. This properly aligns the cutting edge of the outer member window 41 with the rotary cutting edge 42 of the inner distal tip portion 40 and maintains the proper relative axial position therebetween during cutting. Also with the tool 11 installed in the handpiece HP, the diametrical drive pin DP of the handpiece shaft enters and rides in a diametrically opposed pair of the notches 32 of the hub 31 and, upon rotation of the shaft SH, the drive pin DP correspondingly rotates the inner rotatable member 30 and thereby rotates the distal tip portion 40 thereof to rotationally move its cutting edge 42 past the corresponding cutting edges of the outer member window 41.

In various surgical procedures, for example in trimming the edge of the meniscus cartilage in knee surgery, it is often desirable to irrigate with liquid the surgical site (in a conventional manner not shown) and then to draw by suction flowable material (irrigation liquid, bits of removed tissue, etc.) from the surgical site. This can be done by drawing such flowable material into the window 41, then rearwardly along the length of the outer member 11 and further rearwardly through a portion of the hub 31 and then radially outwardly into a suction path through the handpiece and outward therefrom to the suction source S. Thus, the tool 10 can be used for simultaneously cutting tissue at the surgical site and removing flowable material from the surgical site.

To the extent above described, the tool 10 is conventional and one example thereof is shown in above-referenced Cezana et al U.S. Pat. No. 5,192,292.

Unlike in such patent, the intermediate portion 36 of the rotatable inner member 30 comprises a rigid, solid (not hollow) shaft 44 having coaxial front, mid and rear parts 45F, 45M, and 45R of elongate cylindrical form and of diameter sufficiently less than the inside diameter of the sleeve 13 as to create an annular suction passage 46 between the shaft 44 and inside of the sleeve 13 for drawing of flowable materials from a surgical site. The suction passage 46 runs the length of the tool from the distal tip portion 14 of the tubular outer member 11 rearward through the base 12 into the front end of the hub 31 and radially outward therefrom (as hereafter detailed) and through a portion of the handpiece HP indicated by the arrows 46A to the conventional suction source S. In the embodiment shown, the outside diameter of the shaft parts 45F, 45M, and 45R is about ⅔ the inside diameter of the sleeve 13, leaving a substantial radial clearance therebetween for suction of fluid materials from the surgical site.

To rotatably support the shaft for coaxial rotation within the sleeve 13, axially elongate front and rear bushings 50F and 50R respectively are disposed rotatably on reduced diameter parts 51 and 52 of the shaft 44 between the axially spaced shaft parts 45R, 45M and 45R. The shaft parts 51 and 52 are elongate and cylindrical but of diameter less than the shaft parts 45F, 45M and 45R.

Figure 2A:
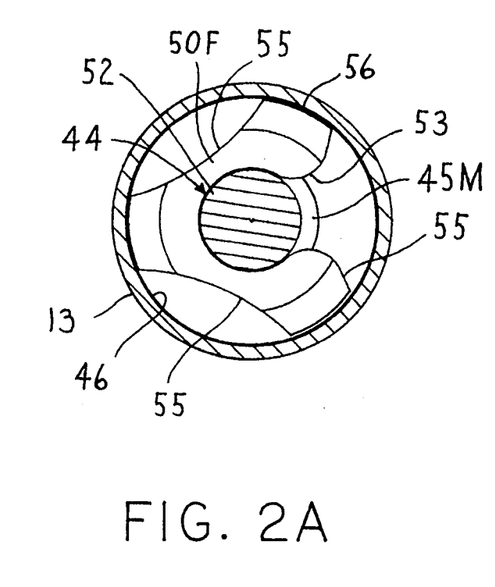
FIG. 2A is an enlarged sectional view taken substantially on the line 2A—2A of FIG. 2.

TO allow the portions 45F, 45M and 45R to be of diameter larger than the shaft parts 51 and 52, the bushings 50 F and R are constructed to snap radially onto the corresponding reduced diameter shaft parts 51 and 52. The bushing 50F applied to the shaft part 52 is shown in FIG. 2A, it being understood that the shaft part 51 and rear bushing 50 are preferably identical. To admit the shaft part 51, 52 radially thereinto, each bushing 50F, R has a slot 53 running axially the length thereof and opening radially outward to the interior of the sleeve 13 and inward to a coaxial, circular cross section bore 54 which extends the length thereof and rotatably coaxially supports the corresponding reduced diameter portion 51 or 52 of the shaft 44. The narrowest width of the slot 53 is slightly more than the outside diameter of the corresponding reduced diameter shaft part 51, 52, permitting the bushing to flex circumferentially enough to widen the slot 53 and allow radial snapping of the bushing over the shaft into the coaxially centered relation shown in FIG. 2A.

In addition, the bushings 50F, R have circumferentially distributed channels 55 indenting the perimeter thereof for the length thereof, one of the channels 55 constituting a funnel-like circumferential widening of the slot 53. The channels 55 continue the suction flow passage 46 axially along and past the bushings 50F, R. Preferably the bushings 50F, R each have three circumferentially distributed channels 55, leaving therebetween three evenly circumferentially spaced, radially outwardly extending lobes 56 (FIG. 2A) radially sized and circumferentially shaped to slide, with the shaft, axially forwardly into the sleeve 13 to the location shown in FIG. 2, for rotatably supporting the shaft with respect hereto. The bushings 50F, R are substantially coextensive in length with the corresponding reduced diameter shaft parts 51, 52. The bushings 50F, R are thus axially snugly sandwiched between the shaft front, mid and rear parts 45F, M, R. The bushings 50F, R are preferably of low friction molded plastics material, such as polycarbonate (in one unit partially glass fiber (30%) filled polycarbonate).

The shaft 44 further includes a drive end portion 57 (FIG. 2) which extends coaxially and integrally fixedly rearwardly from the rear shaft part 45R and rearward coaxially beyond the rear end of the hollow base 12 and is coaxially fixed in driven relation in the hub 31. The base 12 and hub 31 are preferably of rigid molded plastics material, such as polycarbonate. The base 12 and hub 31 are conventionally fixed coaxially as by molding on the rear end portions of the sleeve 13 and shaft 44 respectively. The sleeve 13 and shaft 44 are preferably of rigid stainless steel.

Figure 12:
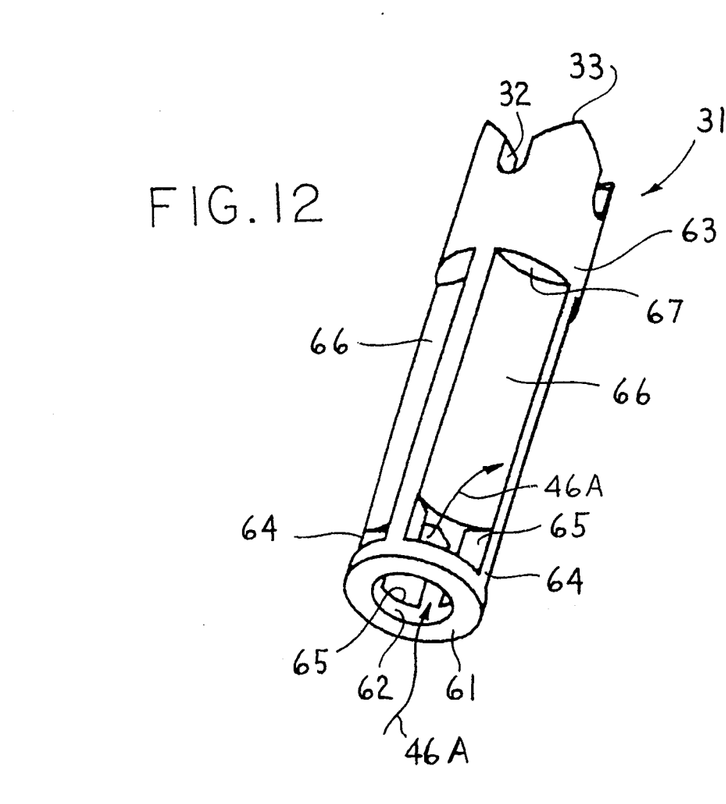
FIG. 12 is a pictorial view of the rotatable drive hub of the FIG. 1 tool.

The hub 31 (FIG. 12) is formed to receive flowable material from the surgical site, and more immediately from the central bore 60 (FIG. 2), and to pass it to the surrounding portion of the handpiece HP for transfer through the suction passage (not shown) in the handpiece to the suction source S. To this end, the front end of the hub 31 defines a ring 61 having a central opening 62 for loosely coaxially receiving therethrough the shaft driven end portion 57 (FIG. 2). The main body 63 (FIG. 12) of the hub 31 is axially spaced from the ring 61 by circumferentially spaced columns 64 defining open windows 65 circumferentially therebetween. The windows 65 open radially outward and also open rearward into corresponding rearwardly extending, correspondingly circumferentially spaced, troughs 66, which end blindly at 67, in spaced relation ahead of the notches 32. Thus, suctioned flowable material from the surgical site passes rearwardly from the central bore 60 of the base 12 (FIG. 2), along the shaft driven end portion 57, through the central opening 62 and more particularly through the annular space between the ring 61 and shaft driven end portion 57, into the flow direction changing space bounded by the columns 64. There the flow is diverted radially outward and rearwardly to flow into the troughs 66 and the portion of the handpiece HP surrounding same, so as to thereafter pass out of the handpiece HP through the suction passage therein (not shown), in the direction of the arrows 46A, to the conventional suction source S.

It will be noted that the shaft rearward driven end portion 57 continues rearward into the main body 63 of the hub 31 (FIG. 2) and abuts a step 68 (FIG. 8) which faces forward from a location adjacent the rear opening recess 34 so that forward pressure on the hub 31 exerts a similar forward pressure against the shaft 44.

Turning now more particularly to aspects of the tool 10 embodying the present invention, attention is directed to FIG. 2.

Under the present invention the distal tip portion 14 (FIG. 2) of the tubular outer member 11 is angled, here at about 15°, with respect to the intermediate portion 15 of the sleeve 13, by reason of an angled portion 70 of the sleeve. The angled portion 70 is smoothly curved as seen in FIG. 2 and the interior of the sleeve maintains its normal circular cross section and diameter from the intermediate portion 15, through the angled portion 70, and into the distal end portion 14. The smooth curvature of the angled portion 70 is achieved by drawing its central length axis arc on a relatively long radius, for example 6 to 8 times the outside diameter of the sleeve 13.

Figures 3, 8, 9, 10, 11:
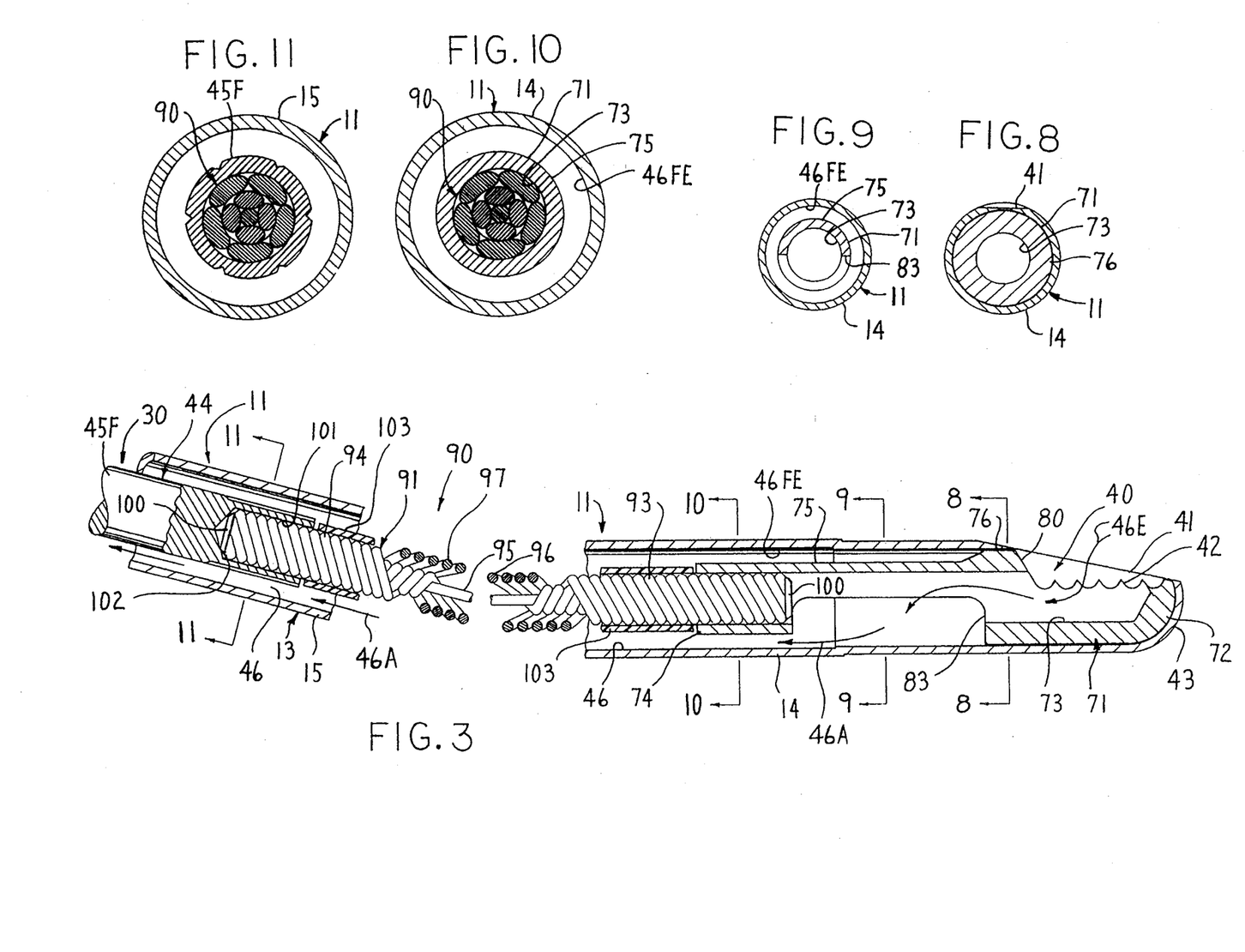
FIG. 3 is an enlarged fragment of FIG. 2 with the rotatable inner member shown in central cross section.
FIG. 8 is a sectional view substantially taken on the line 8—8 of FIG. 3.
FIG. 9 is a sectional view substantially taken on the line 9—9 of FIG. 3.
FIG. 10 is an enlarged sectional view substantially taken on the line 10—10 of FIG. 3.
FIG. 11 is an enlarged sectional view substantially taken on the line 11—11 of FIG. 3.
Figure 3A:
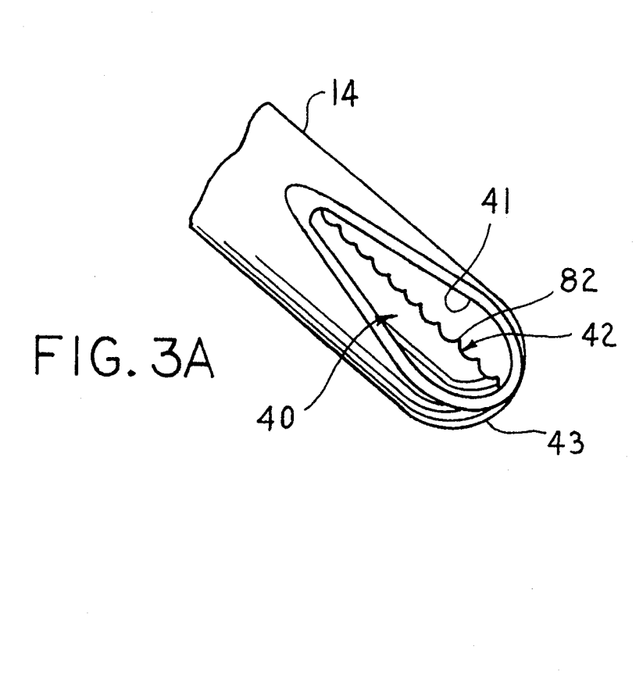
FIG. 3A is a fragmentary pictorial view of the angled distal tip portion of the FIGS. 1-3 tool.

The distal tip portion 40 (FIGS. 2 and 3) of the inner rotatable member 30 comprises a tissue working head 71. The head 71 has a substantially modified bullet shape and indeed can be conveniently manufactured from a bullet shaped blank. The head 71 has a convexly rounded nose 72 which snugly rotates within and bears axially forward on the inner face of the convexly rounded front end 43 of the distal tip portion 14 of the tubular outer member 11. The nose 72 and front end 43 are both preferably hemispherical, as shown. A central bore 73 is a conveniently drilled coaxially in the rear end 74 of the head 71 and extends coaxially forward to the nose 72 (FIG. 3). The central bore 73 extends forward from the head rear end 74. Approximately 3/5 of the length of the head 71 is radially relieved to provide a reduced outside diameter and wall thickness, cylindrical, substantially tubular tail 75. The tail 75 has about the same outer diameter as the shaft portion 45F and is thus radially surrounded by an annular front extension 46FE of the suction passage 46. The head 71 is thus left with a forward radial bearing portion 76, ahead of the front end of the tail 75, namely ahead of the forward extension 46FE of the suction passage and behind the window 41 in the tubular outer member 11. This bearing portion 76 coaxially rotatably supports the head 71 within the distal tip portion 14 of the tubular outer member 11.

Figure 4:
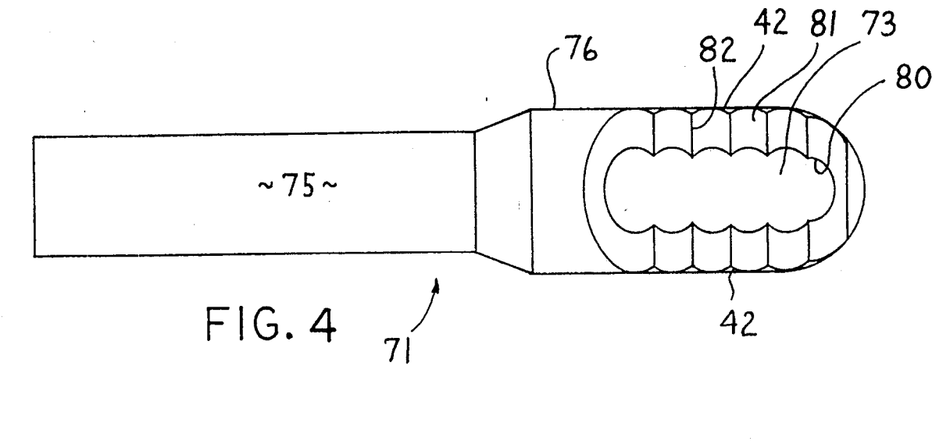
FIG. 4 is an enlarged plan view of a preferred rotatable inner member head of the tool of FIGS. 1-3.
Figure 5:
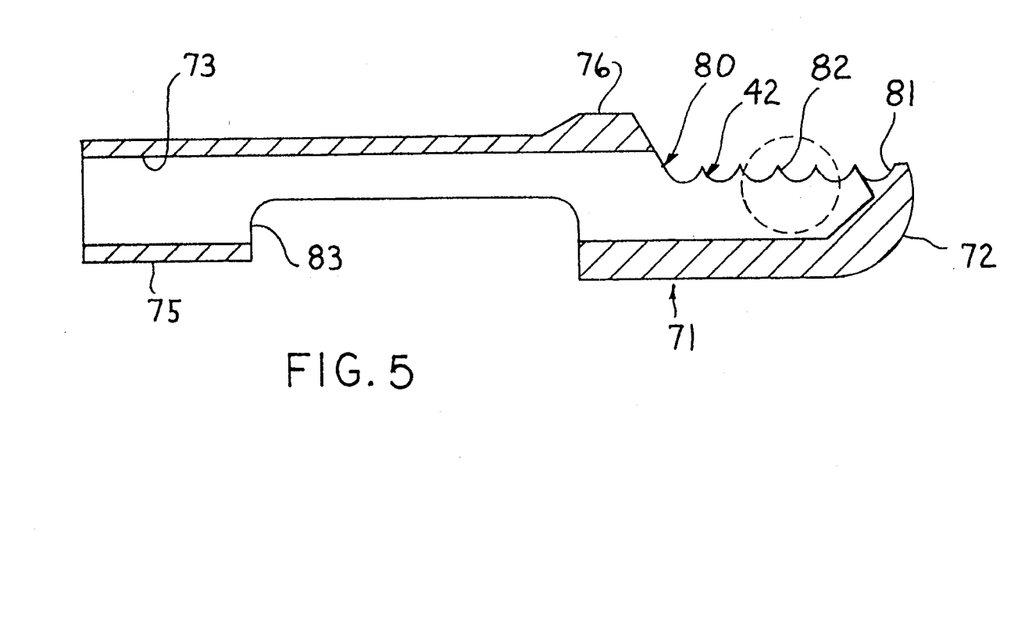
FIG. 5 is a central cross sectional view substantially taken on the line 5—5 of FIG. 4.
Figure 6:
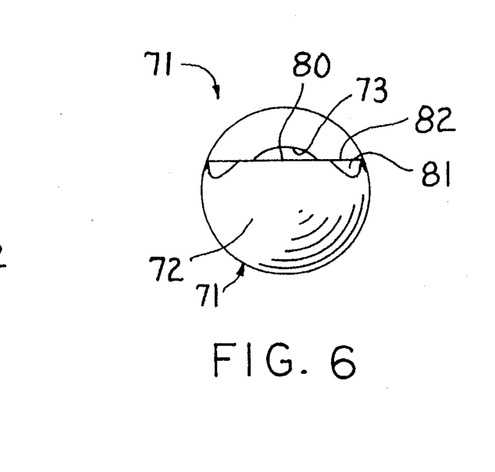
FIG. 6 is a distal end view of the FIG. 4 head.
Figure 7:
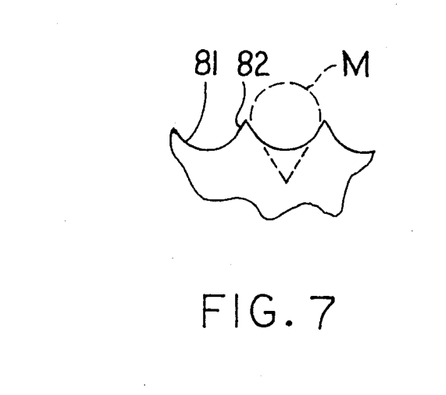
FIG. 7 is a fragment of FIG. 5 showing a preferred tooth form.

To define the cutting edge 42 of the inner rotatable member 30, a circumferential portion (the upper circumferential portion with the head oriented rotatably as shown in FIG. 3) is removed in any convenient way, for example by milling with a relatively small diameter milling cutter of circular cylindrical shape generally indicated in dotted lines at M in FIG. 7. Thus, as indicated in more detail in FIGS. 4–6, successive applications of the milling cutter M here leave an upward opening mouth 80 in relatively large area communication with the central bore 73 of the head 71. In the embodiment shown, the mouth is thus defined by a series of upwardly concave, transversely extending, semi-circular cross section grooves 81 arranged side by side along a substantially chordal plane from the rearward end to the forward end of the mouth 80 and defining the transversely opposed pair of cutting edges 42 on transversely opposite sides of the mouth 80 which in profile, as seen in FIG. 5, provide an appearance of a series of teeth 82. Although the mouth 80 here shown is structured to effectively cooperate its cutting edges 42 in an efficient shearing manner with the adjacent edges of the window 41 of the tubular outer member 11, it will be understood that other types of tissue working cooperation, and structure therefore, may be provided in place of the particular window 41 and mouth 80 here shown. However, the head 71 provides a path for fluent material, including bits of tissue and the like, to be drawn from the surgical site outside the distal portion 14 of the outer tubular member 11 and into the central bore 73 of the head 71, as generally indicated by the further arrows 46E entering the central bore 73 through the window 41 and mouth 80 in FIG. 3, from the surgical site.

A transverse, chordal (here substantially diametral) flow port 83 (FIG. 3) is formed (preferably milled) in the forward end of the tubular tail 75. The port 83 is here about the same axial length as the nose portion of the head extending forward therefrom, and about twice the axial length of the residual portion of the tail 75 extending rearward therefrom. The flow port 83 provides large area communication with the central bore 73. Thus, the port 83 allows relatively free flow of flowable materials therethrough from the mouth 80 rearwardly and radially outwardly into the annular flow passage 46 which extends rearward within the tubular outer member 11 as above described.

The rotatable elongate inner member 30 further includes a coaxial flexibly bendable portion 90 (FIG. 3) coaxially fixed at its opposite ends to the front end of the shaft front part 45F and to the rear end 74 of the head 71 for rotatably driving the head 71 from the shaft 44 and allowing the shaft 44 to axially press the nose 72 of the head 71 forwardly against the rounded front end 43 of the tubular outer member 11. This keeps the mouth 80 in axially correct position with the window 41 while yet allowing bending of the rotatable inner member 30, in the manner seen at FIG. 2, during rotation of the rotatable inner member, despite angling of the distal tip portion 14 with respect to the intermediate portion 15 of the tubular outer member 11 and without scuffing of the rotatable inner member 30 with respect to the surrounding angled portion 70 of the tubular outer member 11. As to the latter, the flexible bendable portion 90 is to be maintained, during rotation, coaxial with the generally curved surrounding angled portion 70 of the outer tubular member and hence so as to maintain a constant thickness annular space therebetween during rotation, as generally indicated in FIG. 2. Further, the member 90, while flexibly bendable during rotation is non-twistable so as to transmit the necessary rotational driving torque from the handpiece HP to the head 71.

In the preferred embodiment shown, the flexibly bendable portion 90 (FIG. 2) comprises an elongate flexible member 91 having a central part 92 located within the angled portion 70 of the tubular outer member 11 and wherein bending during rotation occurs to accommodate the angle of such angled portion 70. The flexible member 91 further includes elongate distal and proximal parts coaxially flanking the central part 92 and respectively extending coaxially into fixed coaxial driving engagement with the adjacent rear and front ends of the head 71 and shaft 44.

In the preferred embodiment shown, the flexible member 91 comprises length of conventional wound-wire flexible shafting. In one unit constructed according to the present invention, the flexible member 91 was a 0.070 inch diameter, 1.65 inch long piece of flexible shafting constructed of stainless steel wire, and available from Suhner Manufacturing Inc. of Rome, Ga. under part No. A-225-4784. That particular unit is shown in FIG. 3 wherein the flexible member 91 comprises a coaxial center wire 95, wound with a first layer of intermediate wound wires 96 (here four in number) in one circumferential direction, which first circumferential layer is then over wound with a second layer of outer wound wires 97 (here five in number). To prevent unwinding of the wires, the ends of the flexible member 91 are here fused by welding as generally indicated at 100. The intermediate and outer wires are tightly wound in a conventional manner.

The end portions of the distal and proximal parts 93 and 94 of the flexible member 91 are coaxially connected to the head 71 and shaft 44 preferably by snug coaxial reception in the rear end portion of the central bore 73 of the head 71 and in a forward facing cylindrical recess 101 (FIG. 3) in the front end of the shaft 44. Actual fixing of the thus inserted ends of the flexible member 91 can be in any conventional manner. It is convenient to crimp the surrounding front end portion of the shaft 44 tightly to the proximal end portion 94 of the flexible member 91 as indicated at 102 in FIG. 3. The same can be done with respect to the distal end portion 93 housed in the head 71 although adhesive bonding, welding or the like may be used instead.

In the preferred embodiment shown, the entire portion of the flexible member 91 between the shaft 44 and head 71 is preferably snugly covered by a relatively thin-walled sheath 103 (FIG. 3). The sheath 103 prevents particles in the suctioned flowable material from entering between the coils of the outer wire layer 96 as the flexible member 91 flexes during rotation. Thus, a solid particle entering between adjacent wire coils on the outside of the bend cannot interfere with contact between such coils on the inside of the bend, following 180° of shaft rotation. In addition, the sheath 103 can act as a buffer preventing direct contact between the outer wires 96 of the flexible member 91 and the inside wall of the angled portion 70 of the tubular outer member 11, in the highly unlikely event of a malfunction wherein the flexible member 91 displaces radially sufficient to brush against the inside surface of the outer tubular member.

In the embodiment shown, the sheath 103 is conveniently a length of conventional heat shrink tubing, preferably polyester heat shrink tubing. This material is relatively low friction material and is capable of shrinking almost half diameter upon application of modest heat thereto, so as to snugly grip the outside of the flexible member 91. The sheath covered flexible member 91 has an effective outside diameter no more than that of the shaft 44 and tail 75 of the head 71, so as to continue the annular passage 46 axially therepast and not impede rearward flow of flowable material from the surgical site therepast.

Applicant has found that the flexible member 91 (FIG. 2) will maintain its coaxial location within the angled portion 70 of the outer tubular member and hence maintain equal radial spacing therein during rotation in surgical use at substantial rotational speeds, for example as high as about 3,000 to 6,000 rpm, given that the head 71 is held forwardly against the front end 43 of the outer tubular member and with substantial axial extension of distal and proximal parts 93 and 94 of the flexible member axially beyond the angled portion 70 of the outer tubular member. In one unit constructed according to the invention, and as shown in FIG. 2, the distal and proximal parts 93 and 94 of the flexible member occupy the straight parts of the outer tubular member flanking the angled portion 70 and are each at least as long as the central part 92 of the flexible member. The central part 92 occupies the angled portion 70 of the outer tubular member and hence is the part called upon to flex during rotation. In other words, the flanking distal and proximal parts 93 and 94 need not flex and are at least as long as the flexing central part 92 which they flank. Further, the coaxially fixed engagement of the distal and proximal parts 93 and 94 of the flexible member 91 with the opposed ends of the head 71 and shaft 44, which are coaxially rotatable within their corresponding portions of the outer tubular member 11, maintain the distal and proximal parts 93 and 94 of the flexible member 91 coaxial within the outer tubular member during rotation.

OPERATION

The tool 10 is readily manufacturable as follows, for example. Following formation of hemispherical distal tip portion 14 and angled portion 70 of the outer tubular member 11, the base 12 is formed and fixed thereto. As to the rotatable inner member, the shaft 44 and head 71 are formed as shown and the hub 31 is formed and fixed on the rear end portion of the shaft 44. The coil compression spring 35 may at any time be inserted into the rear facing recess 34 in the rear end of the base 12. The outer wrapped wire layer 93 of the flexible central portion 92 of the flexible member 91 is loosely sleeved over with the tubular heat shrinkable sheath 103 and its ends are fixedly telescoped in the proposed ends of the shaft 44 and head 71. Thereafter, gentle heating of the shrink tube sheath 103 radially shrinks it to tightly grip the outer wire layer 93 of the flexible member 91 throughout its exposed length. The molded plastic bushings 50R and 50F are radially resiliently snapped onto the reduced diameter shaft portions 51 and 52 respectively so as to rotate freely and coaxially thereon.

Thereafter, the tool 10 can be assembled by insertion of the rotatable inner member 30, head 71 first, forwardly into the rear end of the tubular outer member 11. This telescoping insertion proceeds most easily with the window 41 and mouth 80 facing in the same circumferential direction, for example both facing up with the tool 10 horizontal.

During insertion of the rotatable inner member 30 into the tubular outer member 11, the chamfered forward ends of the bushings 50F, R slide axially therewith, in a low friction manner, forward into their positions shown in the tubular outer member 11 and the head 71 comes axially to press against the closed front end 43 of the outer tubular member 11. The flexible member 91, during such telescoping assembly, accommodates the curvature of the angled portion 70 of the outer tubular member since, while it is laterally bendable it is not axially compressible.

The tool 10 is rearwardly inserted into the chuck C of a handpiece HP in a conventional way, namely by telescoped insertion rearwardly thereinto of the drive hub 31 and outer member base 12. Upon completion of insertion, the split ring 23 and pin 22 of the chuck C axially and radially fix the outer tubular member 11 with respect to the handpiece HP, and the handpiece shaft SH and double pin DP respectively resiliently push forward the resilient inner member distal tip portion 40 against the closed front end 43 of the outer tubular member and insert into opposed notches 32 of the hub 31 to rotatably drive the rotatable inner member upon conventional actuation of the motor means of the handpiece.

To use the tool 10, chucked in a suitable handpiece HP, the handpiece is connected to a suitable power source P (e.g. electric power source) for electric motor MM, and normally to a suitable suction source S. The surgeon can then insert the distal tip portion 14 of the tool in a small, for example arthroscopic, incision into a surgical site in a patient, for example for arthroscopic trimming of the edge of the meniscus cartilage in a knee joint. The angling of the distal tip portion 14 with respect to the proximal portion of the tool 10 permits the surgeon to reach, and orient the cutting window 41 toward, portions of the surgical site which would not readily be accessible by a straight tool without applying excessive tilting or sideways forces to the tissue of the patient through which the tip of the tool is inserted, or without relocating the tool in a new incision.

Surgeon actuation of the handpiece motor MM rotates the rotatable inner member 30. The flexibly bendable portion 90 (FIG. 2) flexes as needed to maintain coaxiality with the angled portion 70 of the outer tubular member 11, i.e. to maintain its centered position therein shown in FIG. 2, during rotation of the inner member. The flexibly bendable portion 90 cannot straighten because of the axial compression force on the inner tubular member due to its axial entrapment between (1) the spring 35 and the drive shaft SH of the handpiece HP at the proximal end thereof and (2) the rounded, closed front end 43 of the outer tubular member at the distal end thereof. Rotation of the head 71 moves the cutting edges 42 of the inner member in a circumferential shearing manner with respect to the cutting edges defined by the window 41, so as to separate small bits of tissue sequentially from the intended portion of the surgical site.

Typically the surgical site is infused with irrigation liquid, from a suitable conventional source not shown. With the handpiece HP connecting the inner portion of the outer tubular member 11 to the suction source S (FIG. 2) excess irrigation liquid, with bits of tissue and other particulate matter entrained therein, is drawn from the surgical site through the window 41 and repetitively as the head 71 rotates, through the mouth 80 thereof, through the central bore 73 thereof and radially out the port 83 thereof and rearwardly along the annular suction passage 46 surrounding the rotating inner member 30. Such rearward flow is facilitated by the channels 55 between the lobes 56 of the bushings 50F, R and by the radial spacing of the rotatable inner member 30 from the interior wall of the tubular outer member 11. Such flow continues through the loose central opening 62 and radially outward opening windows 65 and troughs 66 of the hub 31 and through the suction passage (not shown) in the handpiece HP to the suction source. Such flow is indicated by the arrows in FIG. 2 and FIG. 3.

The tool 10 is constructed in a relatively inexpensive manner so as to be disposable after a single use (for example after a single surgical procedure), so as to avoid need for subsequent sterilization, the costs thereof, the risk of imperfect sterilization, and the resulting risk of contamination of a second patient by bodily materials of a first.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A powered rotatable surgical tissue working tool for chucking in a powered rotating surgical handpiece, comprising:

a tubular outer member including a proximal base releasably fixable on a powered rotatable surgical handpiece, an elongate tubular sleeve fixed to and extending forwardly from said base, said sleeve having an intermediate portion and a distal tip portion and an angled portion connecting said intermediate portion and distal tip portion so that said distal tip portion is angled off the central axis of said base;

a driven rotatable elongate inner member extending coaxially and rotatably within said tubular outer member, said rotatable inner member having a proximal end portion defining a hub rotatably drivably engageable by a powered surgical handpiece, said rotatable inner member having an intermediate portion supported for rotation within said intermediate portion of said tubular outer member and a distal tip portion, said outer tubular member and inner rotatable member having their respective distal tip portions cooperable for surgically working tissue at a surgical site, said inner rotatable member having a flexibly bendable portion disposed lengthwise between said distal tip portion and intermediate portion of said inner rotatable member and disposed within said angled portion of said tubular outer member, said rotatable inner member being axially located within said tubular outer member for substantially axially fixing said rotatable inner member with respect to said tubular outer member, said flexibly bendable portion being of outer diameter substantially less than the inner diameter of said outer tubular member and being located therein in a radially loose, non-contacting, frictionless manner, said inner member flexibly bendable portion comprises a wrapped outer wire spiral coil, said flexibly bendable member further comprises means surrounding said outer wire spiral coil for preventing accumulation of flowable solids between adjacent segments of said coil, for avoiding metal to metal contact in the unlikely event that said flexible member brushes against the interior of said outer tubular member, and to tightly confine said coil against unwrapping, said surrounding means comprising a smooth outer sleeve of conventional heat shrink material, heat shrunk thereon to snugly grip and fixedly surround same and extending substantially the length thereof from said head to said shaft.

2. The apparatus of claim 1 in which said inner member distal tip portion comprises a substantially bullet shaped head having a central bore extending forwardly through its proximal end and ending adjacent its distal end, the distal portion of said head being relieved to define surgical tissue working means and to communicate same with the forward end of said central bore, the distal end of said flexibly bendable member being fixed within and closing the proximal end portion of said central bore, a lateral port in the midlength portion of said head ahead of said flexibly bendable member end and opening radially outward from said bore to the interior of said outer tubular member adjacent said distal tip portion thereof, said bore and port defining a suction passage in said head.

3. A powered rotatable surgical tissue working tool for chucking in a powered rotating surgical handpiece, comprising:

an elongate tubular outer member having a proximal end portion fixable in a handpiece and having a hollow distal tip portion with an opening thereinto;

an elongate rotatable inner shaft extending coaxially within and rotatable inside said outer member and radially spaced from the inside surface of said tubular outer member by an elongate annular suction passage;

a hollow tissue working head rotatably drivable by and fixed with respect to the distal end of said shaft, said head being rotatable inside said hollow distal tip portion of said tubular outer member, said head comprising surgical tissue working means at the distal end thereof cooperable with said opening in said distal tip portion of said outer member for engaging and removing tissue to the interior of the hollow head from a surgical site during surgery, said head further comprising an annular bearing area proximally of said tissue working means for coaxially rotatably supporting said head in said tube, said head further comprising a lateral port located proximally of said bearing area and opening radially between said head hollow interior and said annular suction passage in said outer tubular member, said head having a reduced radius tail proximally of said port for continuing said annular suction passage of said outer tubular member forward along said tail to said port, said tail extending toward said shaft.

4. The apparatus of claim 3 including a flexibly bendable member fixed at its ends to and between said shaft and head to rotatably drive said head from said shaft, said outer tubular member having an angled portion for angling said hollow distal tip portion with respect to an intermediate portion of said tubular outer member, said flexibly bendable member being located in said angled portion of said outer tubular member, bearing means for substantially coaxially supporting said shaft in radially spaced relation within said tubular outer member, said bearing means having means extending endwise therethrough for continuing said annular suction passage in said outer tubular member axially therepast.

5. The apparatus of claim 4 in which said flexibly bendable member comprises a substantially non-twistable torque transmitting member, said shaft and head having coaxial, opposed entries fixedly receiving therein the proximal and distal ends, respectively, of flexibly bendable member, for transmitting torque from said shaft through said flexibly bendable member to said head.

6. A powered rotatable surgical tissue working tool for chucking in a powered rotating surgical handpiece, comprising:

an elongate tubular outer member having a proximal end portion fixable in a handpiece and having a hollow distal tip portion with an opening thereinto;

an elongate rotatable inner shaft extending coaxially within and rotatable inside said outer member and radially spaced from the inside surface of said tubular outer member by an elongate annular suction passage;

a tissue working head rotatably drivable by and fixed with respect to the distal end of said shaft, said head being rotatable inside said hollow distal tip portion of said tubular outer member., said head comprising surgical tissue working means at the distal end thereof cooperable with said opening in said distal tip portion of said outer member for engaging and removing tissue from a surgical site during surgery, said head further comprising a lateral port opening between said tissue working means and said annular suction passage in said outer tubular member, said head having a reduced radius tail proximally of said port for continuing said annular suction passage of said outer tubular member forward along said tail to said port, a flexibly bendable member fixed at its ends to and between said shaft and head to rotatably drive said head from said shaft, in which the head is substantially bullet shaped but has a central bore extending forwardly through its proximal end and ending adjacent its distal end, the distal portion of said head being relieved to define said surgical tissue working means and to communicate same with the forward end of said central bore, the distal end of said flexibly bendable member being fixed within the proximal end portion of said central bore, said lateral port being in the midlength portion of said head ahead of said flexibly bendable member end and communicating between said bore proximal end and the interior of said outer tubular member adjacent said surgical material working means, said bore and port defining a suction passage in said head.

7. The apparatus of claim 4 in which said angled portion and flexibly bendable member have substantially the same center of curvature and in which said flexibly bendable member follows the central length axis of said angled portion of said outer tubular member, the axial length of said flexibly bendable member substantially exceeding the length of said angled portion of said outer tubular member, said flexibly bendable member having a central part located within said angled portion of said outer tubular member, said outer tubular member having straight parts extending distally and proximally from said angled portion thereof, said flexibly bendable member having distal and proximal parts axially flanking said central part thereof and respectively extending axially into said straight parts of said tubular outer member, and such that only the central part of said flexibly bendable member is required to flex during rotation to accommodate the angle of said angled portion of said tubular outer member, said distal and proximal parts of said flexibly bendable member being free of any need to flex during rotation despite said angling of said angled portion of said outer tubular member, the distal tip portion of said tubular outer member having stop means cooperating with said head for stopping forward advancement of said head with respect thereto, means associated with said shaft for blocking retraction thereof during operation, so as to axially press against the ends of said flexibly bendable member and maintain said flexibly bendable member bent at a substantially constant radial distance from the interior surface of the angled portion of said outer tubular member, the diameter of said flexibly bendable portion being about $\frac{2}{3}$ the interior diameter of said angled portion.

8. The apparatus of claim 3 including a molded plastics base and hub fixed proximally on said outer member and shaft, respectively, for engagement by a handpiece and a molded plastics bushing for rotatably supporting said shaft in said outer member, said molded plastics base, hub, and bushing being at least in part of polycarbonate.

9. A powered rotatable surgical tissue severing tool for connection to a powered rotating surgical handpiece, the tool comprising:
   a base releasably fixable to a handpiece housing and a tube protruding fixedly forward from said base, said tube having an angled portion intermediate its ends and a cutting window adjacent its distal end;
   a hub adjacent said base and rotatable with respect thereto, said hub being releasably engageable with and rotatably drivable by a rotatable chuck of a handpiece, and a shaft extending forward from said hub and fixed thereto for rotation thereby, at least a portion of said shaft extending forwardly beyond said base and radially loosely into said tube toward said angled portion of said tube, an elastically laterally flexible non-tubular torque transmitting member fixed on the forward end of said shaft and radially loosely occupying at least said angled portion of said tube for rotation therein, and a head coaxially fixed to the front end of said flexible member and rotatable radially snugly in the distal portion of said tube beyond said angled portion thereof, said head having cutting means coactive with the cutting window of said tube for cutting patient tissue upon rotative driving of said shaft by a powered handpiece;
   means defining an annular suction path from said head rearward outside said flexible member and shaft and within said tube for suctioning irrigation liquid and cut patient tissue bits from said cutting means rearward toward said base radially within said tube and radially outside said shaft and flexible member, the outside diameter of said shaft and flexible member being substantially less than the inside diameter of said tube to make possible such annular suction path, said head having a suction passage therein from said cutting means thereof through a central portion thereof and out a radial port thereof into said annular suction path;
   proximal bearing means axially fixed on said shaft and axially slidable forwardly into said tube for supporting said shaft at a constant radial distance from the interior of said tube help to define said annular suction path therebetween, said proximal bearing means including axial through passages for permitting rearward suction of irrigation liquid and tissue bits therepast, said head including distal bearing means radially engaging the distal portion of said tube for coaxially rotatably supporting the head in said distal portion of said tube; and
   means urging said shaft axially forward and thereby positively axially fixing said flexible member in said angled portion of said tube with said tool chucked in a handpiece;
   such that said flexible member is positively held spaced out of contact with the interior of said tube at the bent portion of said tube while permitting suction of liquid and cut tissue bits through the length of said tube and outside said rotating flexible member and shaft thereby to provide a high speed rotating suction cutter of angled type.

10. The apparatus of claim 9 in which said angled portion of said tube and said flexible member have substantially the same center of curvature.

11. The apparatus of claim 9 in which the flexible member follows the central length axis of the angled portion of said tube.

12. The apparatus of claim 9 in which the axial length of said flexible member substantially exceeds the length of said angled portion of said tube.

13. The apparatus of claim 9 in which the diameter of said flexibly bendable portion of said inner rotatable member is less than half the interior diameter of said angled portion of said outer tubular member.

14. The apparatus of claim 9 in which said shaft and head both have coaxial, opposed entries fixedly receiving therein the proximal and distal ends, respectively, of said flexibly bendable member, for transmitting torque from said shaft through said flexible member to said head.

15. The apparatus of claim 9 in which said flexible member comprises a relatively stiff but laterally resiliently bendable and substantially axially noncompressible core wire snugly wrapped by a spiral coil of resiliently flexible wire.

16. The apparatus of claim 9 in which said head is sized radially to fit in snug rotative bearing support relation within said distal end of said tube, said head having a reduced diameter tail extending rearward from said port for free flowable material movement from said cutting means out through said port of said head and outside said tail and along said flexible member and shaft for suction removal adjacent the proximal end of said tool.

17. A powered rotatable surgical tissue working tool for chucking in a powered rotating surgical handpiece, comprising:

an elongate outer member having a proximal end portion fixable in a handpiece and having a hollow distal tip portion with an opening thereinto;

a rotatable inner shaft extending coaxially within and rotatable inside said outer member and having at least a portion radially spaced from the inside surface of said tubular outer member by an annular suction passage;

a tissue working head rotatably drivable by and fixed with respect to a distal end of said inner shaft, said head being rotatable inside said hollow distal tip portion of said tubular outer member, said head comprising surgical tissue working means at the distal end thereof cooperable with said opening in said distal tip portion of said outer member for engaging and removing tissue from a surgical site during surgery, said head further comprising a lateral port opening between said tissue working means and said annular suction passage in said outer tubular member, said head having a reduced radius tail proximately of said port for continuing said annular suction passage of said outer tubular member forward along said tail to said port.

18. The apparatus of claim 17 in which said suction passage extends rearward from said head at least substantially the length of said outer member and surrounds said inner shaft at least near the join of said inner shaft to said head.

* * * * *